(12) United States Patent
Uihlein

(10) Patent No.: US 10,478,203 B2
(45) Date of Patent: Nov. 19, 2019

(54) SNARE INSTRUMENT WITH SNARE STRUCTURE FORMED FROM A TUBE SECTION

(71) Applicant: Coloplast A/S, Humlebaek (DK)

(72) Inventor: Bernhard Uihlein, Dettingen (DE)

(73) Assignee: Coloplast A/S, Humlebaek (DK)

( * ) Notice: Subject to any disclaimer, the term of this patent is extended or adjusted under 35 U.S.C. 154(b) by 0 days.

(21) Appl. No.: 15/127,501

(22) PCT Filed: Mar. 10, 2015

(86) PCT No.: PCT/EP2015/054894
§ 371 (c)(1),
(2) Date: Sep. 20, 2016

(87) PCT Pub. No.: WO2015/139998
PCT Pub. Date: Sep. 24, 2015

(65) Prior Publication Data
US 2017/0143357 A1     May 25, 2017

(30) Foreign Application Priority Data
Mar. 21, 2014    (DE) .................. 10 2014 205 366

(51) Int. Cl.
*A61B 17/22*     (2006.01)
*A61B 17/221*   (2006.01)
(Continued)

(52) U.S. Cl.
CPC ...... *A61B 17/221* (2013.01); *A61B 17/00234* (2013.01); *A61F 2/01* (2013.01);
(Continued)

(58) Field of Classification Search
CPC .............. A61B 17/32056; A61B 17/22; A61B 17/22031; A61B 17/221;
(Continued)

(56) References Cited

U.S. PATENT DOCUMENTS 7,101,379 B2    9/2006   Gregory, Jr et al.
7,744,604 B2    6/2010   Maitland et al.
(Continued)

FOREIGN PATENT DOCUMENTS

CN    102186427 A       9/2011
DE    197 22 429 A1    12/1998
(Continued)

OTHER PUBLICATIONS

International Search Report (PCT/ISA/210) issued in PCT Application No. PCT/EP2015/054894 dated May 11, 2015 with English translation (seven pages).
(Continued)

*Primary Examiner* — Melanie R Tyson
(74) *Attorney, Agent, or Firm* — Coloplast Corp., Coloplast A/S; Nick Baumann

(57) ABSTRACT

A snare instrument has a snare structure which is formed in one piece from a tube section, by the latter being slit and bent open, and which has a proximal base portion and, extending axially forward from the latter, a distal snaring portion, and which is movable between a snaring position, in which it is moved forward out of an enclosure with the snaring portion folded open, and a securing position, in which it is moved back at least partially into the enclosure with the snaring portion folded in and providing a securing action. The snaring portion, in the folded-open state, has a cup shape with a distal snare opening. For this purpose, a distal end area of the tube section is provided with open axial slits of suitable length introduced from the direction of the distal end of the tube section, and, lying between these, with associated closed axial slits which terminate at a distance in front of the distal end of the tube section and are of greater length than the open axial slits. By way of the open and closed axial slits, wire sections are formed from the tube
(Continued)

section and, when the tube section is bent open, the wire sections form circumferential portions of the snare opening.

11 Claims, 3 Drawing Sheets

(51) Int. Cl.
    *A61F 2/01*     (2006.01)
    *A61B 17/00*     (2006.01)
    *A61B 90/00*     (2016.01)

(52) U.S. Cl.
    CPC ........... *A61B 2017/00358* (2013.01); *A61B 2017/00526* (2013.01); *A61B 2017/00867* (2013.01); *A61B 2017/00902* (2013.01); *A61B 2017/2215* (2013.01); *A61B 2090/3954* (2016.02)

(58) Field of Classification Search
    CPC .. A61B 2017/22035; A61B 2017/2215; A61B 2017/00358; A61F 2/01; A61F 2/013; A61F 2002/018
    USPC .......................................... 606/113, 127, 200
    See application file for complete search history.

(56) References Cited

U.S. PATENT DOCUMENTS

| | | | |
|---|---|---|---|
| 2003/0181942 A1* | 9/2003 | Sutton | A61B 17/0057 606/200 |
| 2003/0187495 A1 | 10/2003 | Cully et al. | |
| 2005/0033334 A1 | 2/2005 | Santra et al. | |
| 2005/0165441 A1* | 7/2005 | McGuckin, Jr. | A61F 2/01 606/200 |
| 2005/0165442 A1 | 7/2005 | Thinnes, Jr. et al. | |
| 2006/0009785 A1 | 1/2006 | Maitland et al. | |
| 2007/0239262 A1 | 10/2007 | Kula | |
| 2008/0311318 A1 | 12/2008 | Uihlein | |
| 2009/0112244 A1* | 4/2009 | Freudenthal | A61B 17/221 606/167 |
| 2009/0192485 A1 | 7/2009 | Heuser | |
| 2010/0137892 A1 | 6/2010 | Krolik et al. | |
| 2011/0319917 A1 | 12/2011 | Ferrera et al. | |
| 2012/0116496 A1 | 5/2012 | Chuter et al. | |
| 2013/0018387 A1* | 1/2013 | Diamant | A61B 17/221 606/127 |
| 2013/0138138 A1 | 5/2013 | Clark et al. | |
| 2013/0289589 A1 | 10/2013 | Krolik et al. | |

FOREIGN PATENT DOCUMENTS

| | | |
|---|---|---|
| DE | 10 2004 055 375 B4 | 12/2007 |
| EP | 1 809 187 B1 | 9/2011 |
| WO | WO 02/078632 A2 | 10/2002 |
| WO | WO 2007/103236 A2 | 9/2007 |
| WO | WO 2010/034021 A2 | 3/2010 |
| WO | WO 2013/071115 A1 | 5/2013 |
| WO | 2013179137 A2 | 12/2013 |
| WO | 2014008460 A2 | 1/2014 |

OTHER PUBLICATIONS

German-language Written Opinion (PCT/ISA/237) issued in PCT Application No. PCT/EP2015/054894 dated May 11, 2015 (six pages).

\* cited by examiner

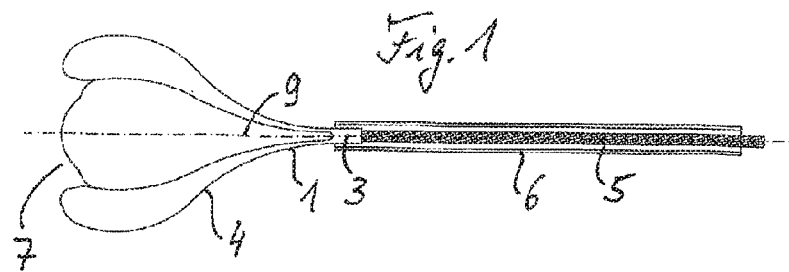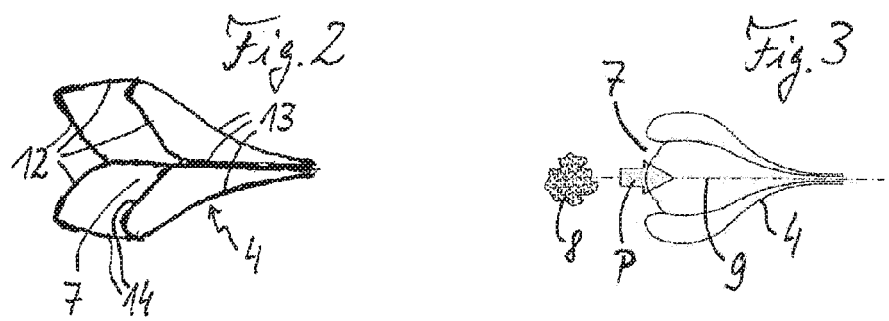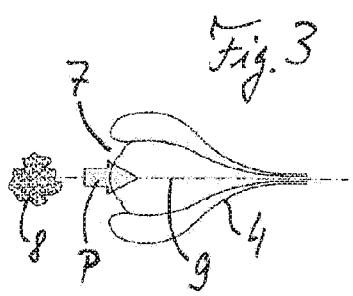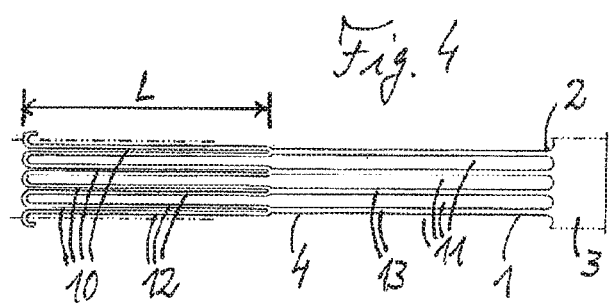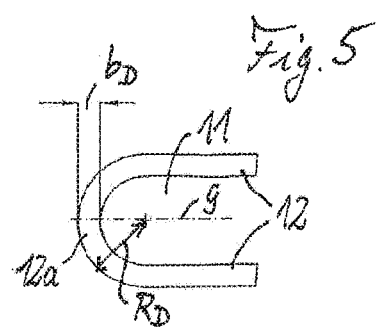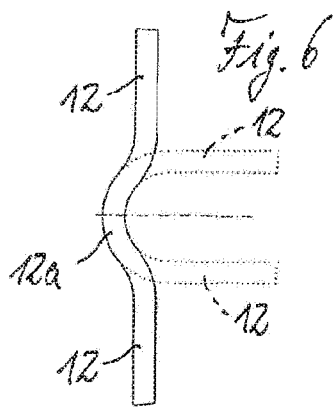

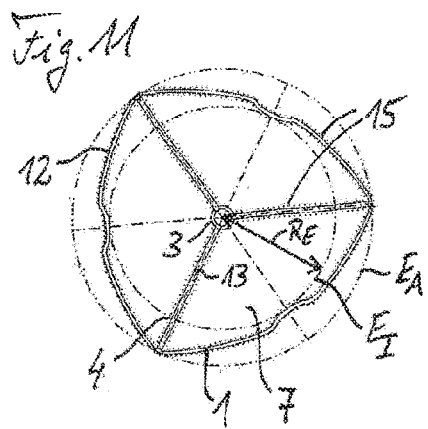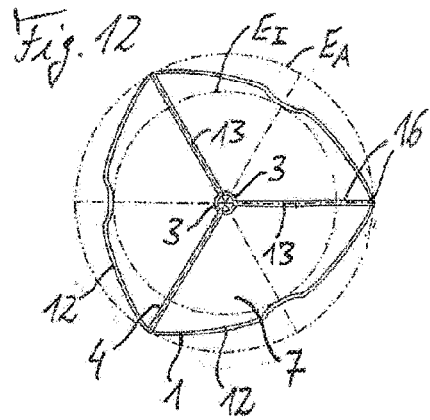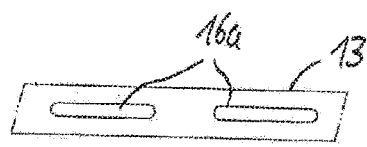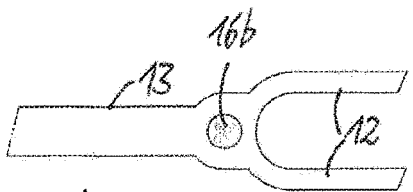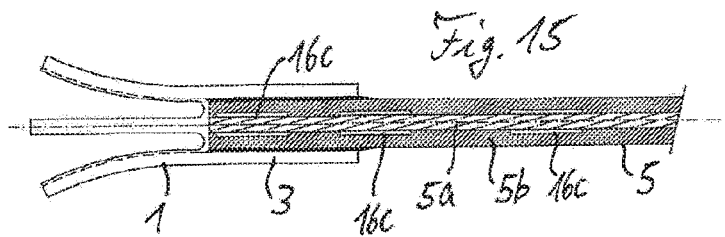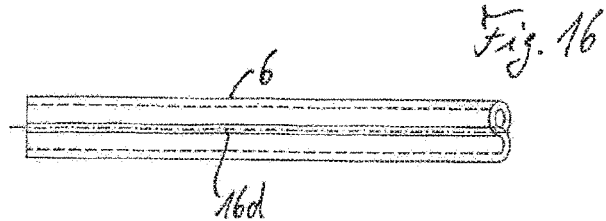

SNARE INSTRUMENT WITH SNARE STRUCTURE FORMED FROM A TUBE SECTION

BACKGROUND AND SUMMARY OF THE INVENTION

The invention relates to a snare instrument with a snare structure which is formed in one piece from a tube section, by the latter being slit and bent open, and which has a proximal base portion and, extending axially forward from the latter, a distal snaring portion, and which is movable between a snaring position, in which it is moved forward out of an enclosure with the snaring portion folded open, and a securing position, in which it is moved back at least partially into the enclosure with the snaring portion folded in and providing a securing action. Snare instruments of this kind are used in particular as medical snare instruments in order to be able to catch and remove foreign bodies, blood clots, stones or other concretions from human or animal tissues, preferably using a corresponding catheter instrument.

In a known type of instrument of this kind, the folded-open snaring portion has a basket shape, i.e. it forms a snaring basket which, in the folded-up state, is received in the enclosure, and which can be moved forward out of the latter, as a result of which it unfolds into its basket shape. Stones and the like can then be maneuvered into the wire basket, transversely with respect to the longitudinal axis thereof, in the area of its maximum diameter and, consequently, maximum opening width. The reason is that, in this area, adjacent wire sections of the basket-forming snare structure are at their maximum spacing, as a result of which corresponding snare openings are formed there on the circumference of the basket. By pulling the wire basket at least partially back into the enclosure, said wire basket is folded inward until it tightly encloses the snared object and thereby secures the latter. The wire basket and the enclosure, along with the snared object, can then be moved out of the tissue channel in question. Stone-collecting basket instruments and balloon catheter instruments of this kind are disclosed, for example, in the patent specification EP 1 809 187 B1 and in the laid-open publication DE 197 22 429 A1.

Another known type of snare instrument of this kind is what is called a snare loop instrument, in which the snare structure is formed from one or more interacting wire loops which can be loose or fixed at the front; see, for example, the laid-open publication WO 02/078632 A2.

The laid-open publication US 2005/0165442 A1 discloses a filter wire structure which is designed to be placed permanently in a tissue channel, in particular in a blood vessel, in order to catch particles or blood clots and thereby prevent embolisms. The filter wire structure is formed in one piece from a tube section, by the latter being slit and bent open, and has a cup shape which terminates at the distal end with V-shaped tips that face forward and slightly radially outward. These distal cup ends, tapering in a V-shape, result from the associated special slitting of the tube section in its outermost distal end portion. Open axial slits introduced from the direction of the distal end of the tube section alternate with closed axial slits which lie between the open axial slits and which terminate at a distance in front of the distal end of the tube section, wherein the open and the closed axial slits, in an axially overlapping area, are about the same width and considerably narrower than the wire sections thus formed between the slits from the tube section. At the distal end, the open slits extend forward with conical widening, such that the radius of an area of curvature, via which in each case two of the wire sections are joined together at the distal end, is at most approximately as large as the width of the wire sections there. The forwardly tapering V-shape of these wire section connections is thus retained even after the filter wire structure has been bent open.

It is an object of the invention to provide a snare instrument which is of the type mentioned at the outset and which offers a good snaring function and a high degree of functional reliability and can be produced with relatively little outlay.

The invention achieves this object by providing a snare instrument comprising a snare structure which is formed in one piece from a tube section, by the latter being slit and bent open, and which has a proximal base portion and, extending axially forward from the latter, a distal snaring portion, and which is movable between a snaring position, in which it is moved forward out of an enclosure with the snaring portion folded open, and a securing position, in which it is moved back at least partially into the enclosure with the snaring portion folded in and providing a securing action. In this snare instrument, the snaring portion, in the folded-open state, has a cup shape with a distal snare opening. Here, a snare opening is to be understood as the area of the maximum opening width of the snare structure, which area is intended and designed to allow objects snared therethrough to pass into the interior of the snare structure. For this purpose, a distal end area of the tube section, which is used to produce the snare structure, is provided with open axial slits of suitable length introduced from the direction of the end of the tube section, and, lying between these, with closed axial slits which terminate at a distance in front of the distal end of the tube section, wherein the closed axial slits are of greater length than the open axial slits and therefore extend in the proximal direction beyond the open axial slits. The remaining tube section areas between the open and closed axial slits form wire sections which, by means of the tube section being bent open, form circumferential portions of the snare opening. When necessary, the snaring portion can be fully folded inward or contracted from its folded-open, cup-shaped state back to a shape corresponding to the tube section when the snare structure is moved completely back into the enclosure.

With the snare instrument according to the invention, stones or other particles in body tissues can be advantageously snared from the front, i.e. they pass from the front in the axial direction through the distal snare opening into the snaring portion that has folded out into a cup shape. For this purpose, the snare structure can be correspondingly moved axially forward. In this way, particles located in the distal direction near a vessel wall can also be snared without any problem. The instrument according to the invention can also be used in the manner of a filter or stent to snare and remove foreign bodies from blood streams and other vessels of the body.

The snare instrument according to the invention can be produced with relatively little outlay since its snare structure is formed in one piece from a tube section which, for this purpose, is slit and bent open in a manner known per se. Welding points for the connection of wire sections can be dispensed with. Since the slits opening out at the distal end of the tube section have a suitable length, the wire sections, which are formed from the tube section by the open and closed axial slits in the axial overlapping area thereof, can form the circumference of the snare opening, i.e. the distal edge of the cup structure of the folded-open snaring portion. Thus, the circumferential length and therefore also the snaring cross section or opening width of the snaring cup can be predefined by the length of the open axial slits. With a greater length of the open axial slits, the circumferential length and therefore the snaring cross section of the snaring cup can be increased. Since the closed axial slits extend proximally beyond the open axial slits, they divide the tube section, in the proximal area behind the open axial slits, into rear wire sections which, in the folded-open state, form a cup body for the snaring cup, and, as has been mentioned, this cup body, at its distal end, terminates with the cup edge formed by the front wire sections. Each rear wire section thus branches into two front wire sections.

In a development of the invention, two adjacent front wire sections, formed from the tube section by the open and closed axial slits, are in each case joined together via an area of curvature, of which the radius $R_D$ is at least as great as two and a half times a width $b_D$ of the wire sections in the area of curvature, i.e. $R_D \geq 2.5 \times b_D$. It has been found that, with this dimensioning, the wire sections are able to bend open very advantageously to form the cup edge, without any danger of breaking, wherein edge areas of the cup tapering to a tip that could cause risks of tissue injury during use are avoided.

In a development of the invention, a circumferential length U of the snare opening is 70% or more of the product of the number 2n of the wire sections formed from the tube section by the open and closed axial slits, multiplied by the length L of the open axial slits, i.e. $U \geq 0.7 \times 2$ nL. This dimensioning permits the provision of a comparatively large snaring cross section with a cup edge which, in the axial direction, has V-shaped portions with obtuse angles and not acute angles.

Depending on the bending-open process used, it is possible, in a development of the invention, to obtain different cup shapes of the snaring portion in the folded-open state, with areas in which the cup diameter increases linearly, progressively or degressively in the distal direction.

In a development of the invention, a maximum cross section of the cup shape of the snaring portion in the folded-open state is greater than a cross section of the snare opening. In certain applications, this can make it easier to secure a snared particle in the snaring cup that has been folded inward.

In a development of the invention, the snaring portion comprises further, second closed axial slits in the tube section, which slits extend forward with their distal end at the level between a distal and a proximal end of the first closed axial slits and rearward with their proximal end behind the proximal end of the first closed axial slits. This permits a wire-branching configuration of the cup body formed in this case by the first and second closed axial slits.

In a development of the invention, the snare structure and/or the enclosure and/or a pulling wire guided axially movably in the enclosure for the snare structure is provided across the whole surface or a partial surface, or at points, with a magnetic resonance (MR) marker material. This permits an advantageous use of the snare instrument in corresponding MR applications, since its snare structure is visible under MR.

BRIEF DESCRIPTION OF THE DRAWINGS

Advantageous embodiments of the invention are shown in the drawings and are described below. In the drawings:

FIG. 1 shows a schematic longitudinal sectional view of a snare instrument with a cup-shaped snaring portion, FIG. 2 shows a perspective view of a snaring portion of a snare structure of the instrument from FIG. 1, FIG. 3 shows a schematic side view of the snaring portion from FIG. 2 in order to explain a process by which particles are snared, FIG. 4 shows a developed view of a tube section that has been slit for the snare structure of the instrument from FIG. 1, FIG. 5 shows a detailed view of a distal wire section connection area of the slit tube section from FIG. 4, FIG. 6 shows the view from FIG. 5 after the slit tube section has been bent open to form the cup-shaped snaring portion, FIG. 11 shows a plan view corresponding to FIG. 7 of another snaring cup, with three instead of four rear cup body wire sections and with an MR marker coating across the whole surface, FIG. 12 shows a view corresponding to FIG. 11 for a variant with MR marker material applied across a partial surface and at points, FIG. 13 shows a detailed view, from FIG. 12, of an area with MR marker material across a partial surface, FIG. 14 shows a detailed view, from FIG. 12, with MR marker material applied at points, FIG. 15 shows a detailed sectional view of the instrument from FIG. 1 with MR marker material in a shaft area, and FIG. 16 shows a side view of an enclosure with MR marker material, as can be used for the instrument from FIG. 1.

DETAILED DESCRIPTION OF THE DRAWINGS

Figure 7:
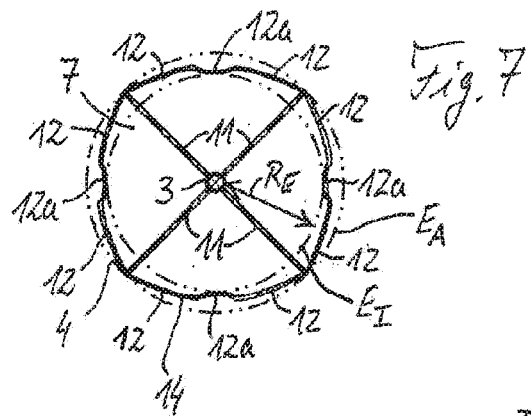
FIG. 7 shows a plan view of the cup-shaped snaring portion from the front.

The snare instrument shown in FIGS. 1 to 7 has a snare structure 1 which is formed in one piece from a tube section 2, by the latter being slit and bent open, shown in its developed view in FIG. 4. The snare structure 1 comprises a proximal, unslit base portion 3 and, extending axially forward from the latter, a distal snaring portion 4.

At its proximal end area, the snare structure 1 is coupled to a distal end area of an actuation element 5 which is designated as a pulling wire and which is guided axially movably in an enclosure 6. The coupling is preferably configured in such a way that the proximal end area of the snare structure 1 is connected permanently to the distal end area of the actuation element 5 so as to be rigid in terms of axial movement, e.g. by an adhesive or welded connection. In this way, the snare structure 1, by means of corresponding axial actuation movement of the actuation element 5, can be moved both axially forward and also axially rearward. Pulling wire 5 and enclosure 6 are preferably made from an elastically bendable material. In FIG. 1, the snare structure 1 is shown in a snaring position in which it is moved forward completely out of the enclosure 6, and the snaring portion 4 adopts a fully folded-open state. By pulling the pulling wire 5 back and/or pushing the enclosure 6 forward, the snare structure 1 can be drawn completely into the enclosure 6, whereupon its snaring portion 4 contracts, i.e. folds inward to the internal diameter of the enclosure 6. In this fully folded-in position, the snaring portion 4 adopts more or less the initial configuration shown in FIG. 4, as exists after the slitting and before the bending open of the tube section 3. The techniques for slitting and bending open the tube section 3, for the purpose of obtaining the snare structure 1, are familiar to a person skilled in the art. For the snare structure 1, suitable materials are used which bend open elastically and, in the bent-open state, can be fixed elastically by a treatment process such as baking or hardening. For example, super-elastic materials such as NiTi alloys are customary for this purpose.

As can be seen in particular from FIGS. 1 to 3, the snaring portion 4, in the folded-open state, has a cup shape with a distal snare opening 7, which at the same time represents the maximum opening width of the snare structure 1. Accordingly, this snare instrument is used in medical applications, for example as an instrument for snaring stones, in order to maneuver stones, or other particles in the body tissue of a patient, into the snaring portion 4 from the front. This distinguishes the instrument from conventional basket-type snare instruments in which the particles are snared transversely with respect to the longitudinal axis of the instrument, i.e. in the radial direction, into a wire basket that is substantially closed at the front and rear.

FIG. 3 illustrates a particle 8, e.g. a kidney stone, being snared in this way from the front, through the snare opening 7 and in a proximal direction P parallel to a longitudinal axis 9 of the instrument and therefore also of the cup-shaped snaring portion 4. This can facilitate the snaring process by comparison with instruments having a basket closed at the front and rear since, for the snaring process, the instrument basically only has to be moved axially and not in the transverse direction. Moreover, this can make snaring of particles easier in cases where the particles are located axially in front of and close to a vessel wall lying behind them.

As can be seen in particular from FIGS. 2 and 4, the tube section 2, during slitting, is provided with a special slit structure which, at the distal end of the tube section, comprises open slits 10 and, lying between these, closed axial slits 11 which terminate at a distance in front of the distal end of the tube section. The closed axial slits 11 extend in the proximal direction rearward beyond the distally open slits 10. By means of this slit structure, first, front wire sections 12 and second, rear wire sections 13 are formed from the distal portion of the tube section in question. The front wire sections 12 are present here in an axial area in which the open slits 10 and the closed slits 11 overlap, wherein the open and the closed slits 10, 11 alternate in the circumferential direction. The rear wire sections 13 lie in the axial area in which the closed slits 11 extend proximally beyond the open slits 10. Thus, each rear wire section 13 branches into two front wire sections 12 at the transition area.

The distance at which the closed slits 11 terminate in front of the distal end of the tube section defines a wire section width $b_D$ of a curved wire section area 12a, via which each front wire section 12 is joined distally to an adjacent front wire section 12. The wire section width $b_D$ of this curved wire connection area 12a, which is semi-circular in the example shown, can approximately correspond, for example, to the width of the front wire sections 12 connected thereto, as can be seen from FIG. 5. It can also be seen from FIG. 5 that a radius of curvature $R_D$ of this curved wire connection area 12a is substantially greater than the diameter or the width $b_3$ of the wire connection area 12a. The corresponding slitting process ensures that this radius of curvature $R_D$ is at least two and a half times this wire section width $b_D$, i.e. $R_D \geq 2.5 \times b_D$. This has the effect that, when the slit tube section is bent open into the cup shape of the snaring portion 4, the front wire sections 12, in their curved connection area 12a, can be bent open to a desired angle of bending open, which angle can be quite considerable, without any danger of breaks occurring in the wire connection area 12a, and, according to requirements, end contours that taper to a point in the distal direction can be avoided for the snare structure 1. FIG. 6 illustrates, by way of example, the bending-open of two wire sections 12 connected via the connection area 12a, namely from their parallel starting position, represented by broken lines, to a position in which they are bent open to 180°.

The stated slit structure of the tube section 2 has the effect that the snaring portion 4 can be bent open in the desired manner to give the stated cup shape with the distal snare opening 7. As can be seen in FIG. 2, the rear wire sections 13 form a cup body, while the front wire sections 12 form a distal circumferential edge 14 of the snaring portion 4, i.e. the edge of the distal snare opening 7. Thus, the length of the front wire sections 12 and the number of the latter define or limit the maximum length of the distal edge of the snaring cup 4. In other words, the distal open slits 10, as shown in FIG. 4, are introduced in a suitable length L into the tube section 2, which length L is chosen such that the snaring portion 4 can be bent open to the desired cup shape, wherein the length of the cup edge and therefore also the circumference of the effective admission cross section of the admission opening 7 are defined by this length L of the open slits 10, and thus of the front wire sections 12, and also by the extent of bending open of the front wire sections 12 at their wire connection area 12a.

In the example shown in FIG. 4, the slit structure comprises four distally open slits 12 and four closed slits 11 and, consequently, a number n of four rear wire sections 11 and twice as great a number 2n of eight front wire sections 12. It will be appreciated that, in alternative embodiments of the invention, any desired number n of closed or distally open slits can be provided, i.e. the number n can be any desired whole number greater than one.

The stated dimension ratios will be explained in more detail on the basis of the plan view of the snaring cup 4, or of its snaring opening 7, as shown in FIG. 7. As will be seen from FIG. 7 for the illustrative case of a number n=4 of open or closed tube slits and therefore a number n=4 of four rear wire sections 11 and twice as great a number 2n=8 of front wire sections 12, the cup edge 14 is formed by the eight front wire sections 12 plus their four connection areas 12a. Accordingly, the length of this cup edge is approximately eight times the length L of a front wire section 12 plus what is by comparison a much smaller contribution of the four wire connecting areas 12a. The cup edge 14 lies in an axial projection between an inner circle $E_I$ and an outer circle $E_A$, wherein the outer circle $E_A$ defines the external diameter of the snaring cup 4 and the inner circle $E_I$ represents a snare opening circle which, with good approximation, represents the snare opening 7 bordered by the cup edge 14.

If the front wire sections 12 are bent open by ca. 180° at their wire connection areas 12a, as in the example of FIG. 6, this results in a cup edge 4 lying almost in one plane, and the circumferential length of the cup edge 4 is then only slightly greater than a circumferential length U of the snare opening circle $E_I$, which is determined from the radius $R_E$ thereof by the equation $U=2\pi R_E$. In other words, the circumferential length U of this effective snare opening circle $E_I$ is only slightly smaller than the actual circumferential length of the cup edge 4, which circumferential length is given by the product 2 nL from the number 2n of the wire sections 12, 13 formed from the tube section 2 by the open and closed axial slits 10, 11, multiplied by the length L of the open axial slits 10 plus the length contributed by the wire connection areas 12a.

Thus, by choosing a sufficient length L of the distal open slits 10, the snare opening 7 can be made available with a desirably large snaring cross section. If the front wire sections 12 are bent open at their wire connection area 12a by a smaller angle than 180°, an undulating profile of the cup edge 4 is obtained with a smaller bending-open angle, as a result of which the length of the cup edge increases slightly compared to the circumferential length U of the effective snare opening circle $E_I$. In advantageous embodiments, the circumferential length U of the snare opening circle $E_I$ is kept at a value of at least 70% of the product 2 nL from the number 2n of the front wire sections 12 and their length L. This leads to favorable cup shapes of the snaring portion 4, with a comparatively large snare opening 7 and an only moderately undulating profile of the cup edge 14.

Figure 8:
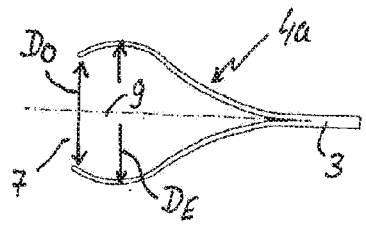
FIG. 8 shows a schematic side view of a snare structure with a diameter of the snaring cup increasing degressively in the distal direction.
Figure 9:
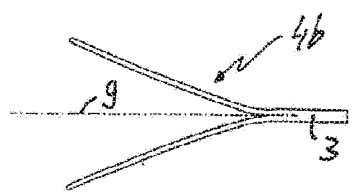
FIG. 9 shows a view corresponding to FIG. 8 for a snare structure with a snaring cup diameter increasing linearly in the distal direction.
Figure 10:
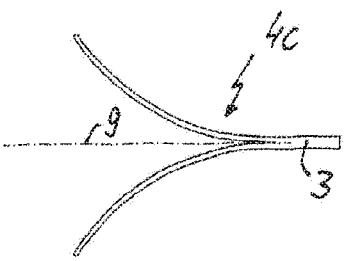
FIG. 10 shows a view corresponding to FIG. 8 for a snare structure with a snaring cup diameter increasing progressively in the distal direction.

Any desired configurations of the snaring cup 4 can be obtained by using a corresponding bending mold introduced, for bending open, into the slit distal area of the tube section. FIGS. 8 to 10 show three representative examples. In the embodiment variant in FIG. 8, the snare structure has a snaring portion 4a, which widens degressively, i.e. weaker than linearly, in the distal direction from the base portion 3. At a distance in front of the distal snare opening 7, it adopts a maximum diameter $D_E$ or cross section, from which it narrows to a slightly smaller diameter $D_O$ or cross section of the snare opening 7. The distal narrowing of the snaring cup 4a can assist the secure holding of a snared object.

In a variant shown in FIG. 9, a snaring cup 4b extends in the distal direction, from the base portion 3, with a linear increase in its widening diameter. In an embodiment variant shown in FIG. 10, a snaring cup 4c extends in the distal direction, starting from the base portion 3, with a progressive increase of its diameter, i.e. stronger than a linear increase. It will be noted that the cup variants of FIGS. 9 and 10 also permit secure holding of a snared object, in that the snaring cup 7 is pulled back into the enclosure 6 until, due to folding-in, it bears tightly against the snared object with its cup wire structure and, by means of static friction, prevents said object from sliding forward and out.

FIGS. 11 to 16 illustrate advantageous configurations of the snare instrument according to the invention which are particularly suitable for MR applications and, for this purpose, are provided with an MR marker material in a manner known per se. In this connection, FIG. 11 shows an example in which the snare structure 1 is coated across its whole surface with an MR marker material 15, as is indicated by stippling of the coated outer surfaces of the snare structure 1.

In the example in FIG. 11, the snaring cup 4 is formed by three rear wire sections 13 and accordingly six front wire sections 12, with corresponding results in terms of the dimensioning of the cup edge 14, with respect to the effective snare opening circle $E_I$ and the outer circle $E_A$ of the snaring cup 4, as have been explained above for the illustrative embodiment of FIG. 7 in the case of n=4 rear and eight front wire sections, to which reference can be made.

FIG. 12 shows a variant of the illustrative embodiment of FIG. 11, with partial surface areas and punctifom areas of the snare structure 1 being provided with an MR marker material 16. The detailed view in FIG. 13 shows a partial surface coating of the rear wire sections 13 by a series of elongate MR marker strips 16a arranged at a distance one behind the other. Alternatively or in addition, corresponding MR marker strips can be provided on the front wire sections 12. FIG. 14 is a detailed view showing a punctifrom MR marker spot 16b, which is placed in each case in the area of the bifurcation where the rear wire section 13 branches into the two front wire sections 12.

FIG. 15 illustrates an embodiment variant in which the pulling wire 5 is formed by a wire core 5a and by a core sheath 5b surrounding the latter, wherein rings 16c of an MR marker material are placed at an axial distance from one another on the wire core 5a and are embedded by the sheath 5b. FIG. 16 shows an embodiment variant in which the tubular enclosure 6, in which the pulling wire 5 is guided in an axially movable manner, is provided with an axially extending, linearly shaped MR marker material 16d. It will be appreciated that the measures mentioned in relation to FIGS. 11 to 16, for providing a desired MR visibility of the snare instrument for MR applications, can be combined with one another in any desired manner.

In embodiments of the invention that are not shown, the snaring cup has a more strongly branched structure in the area of its cup body. For this purpose, in addition to the distally open slits and the closed slits axially overlapping the latter, further closed slits are then introduced into the tube section, wherein these further closed slits axially overlap the closed slits already mentioned and extend beyond these in the proximal direction. Preferably, the further closed axial slits can again alternate with the other closed slits in the overlap area in the circumferential direction. This then results in a lattice-like branched structure of the cup body.

As the above description of advantageous exemplary embodiments makes clear, the invention makes available a snare instrument that can be used in particular as a medical snare instrument, e.g. also in MR applications, and permits reliable snaring of foreign bodies, particles, etc., from the direction of the front. The snare structure is produced here in one piece from a tube section, in a manner that is advantageous from the manufacturing point of view. This does not require the production of special wire connections, such as welding points. Accordingly, there are no problems caused by breakage or other failure of corresponding welding points or adhesive points or other connection points.

The invention claimed is:
1. A snare instrument comprising
    an enclosure; and
    a snare structure placed in the enclosure, where the snare structure is formed by a tube section that extends from a proximal end of a proximal base portion to a distal end of a distal snare portion, the tube section including:
        a plurality of open slits formed in the distal end of the tube section, with each open slit extending a distance L in an axial direction toward the proximal base portion, and
        a plurality of closed wire sections, with each closed wire section located between a first open slit of the plurality of open slits and a second open slit of the plurality of open slits adjacent to the first open slit, where each closed wire section is formed by a channel opening, and the channel opening is spaced a distance Bd away from the distal end of the tube section such that the closed wire section is closed at the distal end of the tube section by a curved wire section, where the curved wire section has a radius of curvature R;

wherein the channel opening is semi-circular and the radius of curvature R of the curved wire section is at least a factor of 2.5 greater than the distance Bd;

wherein the snare structure is movable between a snaring position characterized by the snare structure moved forward in a distal direction out of the enclosure and a securing position characterized by the snare structure moved back in a proximal direction into the enclosure;

wherein, when in the snaring position, the snare structure forms a cup shape having a distal snare opening that is approximately circular;

wherein n is defined as a number of the plurality of open slits, and a circumferential length of the distal snare circular opening is 70% or more of the product of 2 nL.

2. The snare instrument as claimed in claim 1, wherein the cup shape comprises one or more areas in which a diameter increases linearly in the distal direction progressively in the distal direction, or degressively in the distal direction.

3. The snare instrument as claimed in claim 1, wherein a maximum diameter (DE) of the cup shape is greater than the diameter of the distal snare opening.

4. The snare instrument as claimed in claim 1 wherein a length of each of the channel openings of the plurality of closed wire sections is equal.

5. The snare instrument as claimed in claim 1, wherein at least one of the enclosure and the snare structure includes a magnetic resonance (MR) marker material.

6. The snare instrument as claimed in claim 1, wherein the curved wire section has a uniform width equal to the distance Bd.

7. The snare instrument as claimed in claim 1, wherein, when measured at the distance Bd away from the distal end of the tube section, the channel opening is semi-circular.

8. The snare instrument as claimed in claim 1, wherein the distal snare opening of the snare structure is characterized by an absence of end contours that taper to a point.

9. The snare instrument as claimed in claim 1, wherein the channel opening of each closed wire section is characterized by an absence of end contours that taper to a point.

10. The snare instrument as claimed in claim 1, further comprising:
a wire located axially in the enclosure and coupled to the proximal base portion of the tube section.

11. The snare instrument as claimed in claim 1, wherein each of the plurality of closed wire sections includes a first wire section on a first side of the channel opening and a second wire section on a second side of the channel opening, with the first wire section connected to the second wire section by the curved wire section, and the radius of curvature R of the curved wire section being at least the factor of 2.5 greater than the distance Bd configures the first wire section to be disposed at approximately 180 degrees relative to the second wire section at the distal snare opening.

* * * * *